United States Patent [19]

Arimoto et al.

[11] Patent Number: 5,014,009

[45] Date of Patent: May 7, 1991

[54] DETECTOR FOR GAS CHROMATOGRAPH FOR DETECTING AMMONIA AND AMINE COMPOUNDS

[75] Inventors: Hiromi Arimoto, Kyoto; Toshihiro Fujii, Tokyo, both of Japan

[73] Assignee: Shimadzu Corporation, Kyoto, Japan

[21] Appl. No.: 471,675

[22] Filed: Jan. 25, 1990

Related U.S. Application Data

[63] Continuation-in-part of Ser. No. 363,392, Jun. 6, 1989, abandoned, which is a continuation of Ser. No. 22,445, filed as PCT JP86/00245 on May 14, 1986, published as WO86/06836 on Nov. 20, 1986, abandoned.

[30] Foreign Application Priority Data

May 17, 1985 [JP] Japan .................................. 60-106243
Aug. 20, 1985 [JP] Japan .................................. 60-183441

[51] Int. Cl.⁵ .................... G01L 21/32; G01N 30/00
[52] U.S. Cl. .................................. 324/468; 324/464; 73/23.35; 73/23.4
[58] Field of Search .............................. 324/457–459, 324/464, 468, 72.5; 73/23, 23.1, 25, 61.1 R; 361/213; 204/164

[56] References Cited

U.S. PATENT DOCUMENTS 3,589,869 6/1971 Scolnick .......................... 324/464 X
4,345,154 8/1982 Bainbridge ..................... 324/464 X

FOREIGN PATENT DOCUMENTS 2430009 2/1980 France ................................ 324/468
47-6360 2/1972 Japan .
50-61288 5/1975 Japan .
50-128595 10/1975 Japan .
2118306A 10/1983 United Kingdom ............... 324/468

Primary Examiner—Reinhard J. Eisenzopf
Assistant Examiner—Jack B. Harvey
Attorney, Agent, or Firm—Armstrong, Nikaido, Marmelstein, Kubovcik & Murray

[57] ABSTRACT

A detector device for a gas chromatograph, for detecting surface ionization wherein ions will be detected which are formed upon contacting amine compounds and ammonia with the surface of metallic oxides having a large work function. The detector enables detection of poisonous amine compounds and ammonia with high sensitivity.

2 Claims, 4 Drawing Sheets

DETECTOR FOR GAS CHROMATOGRAPH FOR DETECTING AMMONIA AND AMINE COMPOUNDS

This application is a continuation-in-part of application Ser. No. 363,392 filed as PCT JP86/00245 on May 14, 1986, published as WO86/06836 on Nov. 20, 1986 now abandoned which is a continuation of application Ser. No. 022,445, filed Jan. 13, 1987, now abandoned.

DESCRIPTION

1. Technical Field

This invention relates to a device for detecting gases separated in a gas-chromatographic analysis. The invention more particularly relates to a device for selectively and sensitively detecting amonia and amine compounds.

2. Background Art

In detecting presence of amine compounds and ammonia by a gas chromatographic analysis, conventionally applied were detectors of the type of thermal ionization or fluorescence in a post-column or colorimetry, all of these conventional methods are defective or unsatisfactory in terms of selectivity and sensitivity.

For instance, the thermal ionization detector is excellent in detecting nitrogen compounds, but this excellence is justified in the case of detecting all existing nitrogen compounds together and is not justified in selective detection of amine and ammonia compounds contained in other nitrogen compounds. Therefore, it is difficult by a thermal ionization detector to ananlyze only amine compounds. Further, this type lacks sensitivity of "ppb" order and inferior in repeatability, which leads to inadequacy to practical use and, additionally, the thermal ionization type always needs hydrogen gas, which will cause constant danger and demand close attention in analytical works. These are problems unsolved in conventional art.

In the prior art, there has been no selective and sensitive gas chromatographic detector for tertiary amines, secondary amines, and hetero-cyclo amines. However, a thermionic detector (TID, and sometimes referred to as an "N-Detector"), as described above, responds to any compound that includes nitrogen atoms. The ionization mechanism of a TID is different from that of a surface ionization detector (SID), as described below in relation to the instant invention. For example, it is considered that in the TID, the compound which comes to the detector is first decomposed to CN and other parts, and CN ionized, for example:

[TID]PB * +CN→Pb+ +CN−

DISCLOSURE OF THE INVENTION

Substantially, this invention proposes a detector device which is capable of service as a surface ionization detector (hereinafter, noted as SID) which is adapted to detect ions to be formed on a surface of a metal oxide compound having a large work function during contact with amine compounds or ammonia and also serving as a flame ionization detector (hereinafter, noted as FID) which has a popular or standard level of high-sensitivity for organic compounds other than amine compounds or ammonia, wherein a switch in the two alternative applications is readily made. A detector device for a gas chromatograph of the present invention comprises a heated emitter electrode which has at least part of its surface defined of metallic platinum, molybdenum, rhenium or iridium; or oxides of such metals; or a combination of such metals with such oxides; a heater source which will energize and heat the emitter electrode, preferably to 500°-600°C.; a nozzle which is disposed opposite to the emitter electrode; a sample gas flow route communicated to the nozzle; a carrier gas flow route also communcated to the same nozzle; a collector electrode disposed in a proximity of the heated emitter electrode; an opposed electrode disposed to be opposite to the collector electrode; and a DC source which is connected to the collector and the opposed electrodes via an electrometer.

In an SID according to the instant invention, the amonia related compound is directly ionized on the emitter surface. The decomposition process does not occur as in the TID described above. It is considered that the ionization mechanism can be illustrated as follows:

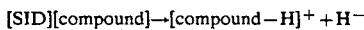

[SID][compound]→[compound−H]+ +H−

(one hydrogen atom is separated from the parent compound).

Then, an SID which as proposed by the present applicant is based on the following principle.

When a gaseous sample of, for instance, amine compounds and oxgen-containing gas (for instance, air) are mixed and directed to contact with a heated solid surface (emitter) comprised of metallic platinum, molybdenum, rhenium or iridium; or combination of such metals and oxides thereof, amine compounds and the like will heat-decompose on the surface to yield chemical species having lower ionization potentials and such chemical species are adapted to form surface ionization on the surface of a metallic emitter which is of a large work function and is also in thermal, electrical equilibrium with the chemical species. Measurement of ionizing current occuring under such conditions will enable detection of amine compounds having lower work function, with outstanding selectivity and sensitivity. Herein, the phenomenon of the surface ionization is explained by use of the following Saha-Langmuir's equation:

$$\frac{n_+}{n_0} = \frac{g_+}{g_0} \exp\left(\frac{\Phi - IP}{KT}\right) \quad (1)$$

wherein $n_+/n_0 = $ a ratio of positive ions to neutral chemical species, $\phi = $ work function on a metallic emitter at a temperature (T) of forming the surface ionization, K = Boltzmann constant, T = surface temperature of the metallic emitter, IP = ionization potential of the chemical species which are ionizing on the surface, $g_+/g_0 = $ the ratio of statistic weights of positive ions to the neutral chemical species. Following the formula above, in most cases, organic compounds tend to decompose on a heated metallic emitter surfaces to be chemical species having lower ionization potential than at original molecules and to be effectively ionized. Herein, ionic current ($i_S(T)$) by positive ions in connection with chemical species (S) which are formed on the metallic emitter surface is given below:

$$i_S(T) = n Y_S(T) \cdot \beta_S(T) \quad (2)$$

wherein T = a temperature of the metallic emitter surface, $\beta_S(T) = $ ionization efficiency, n = number of organic molecules being impinged from gas phase on the surface, $Y_S(T)$ = a yield of chemical reactions on the metallic emitter surface. Further, $\beta_S(T)$ is denoted by the following formula with use of the Saha-Langmuir equation (1).

$$\beta_S(T) = \frac{1}{1 + \frac{g_0}{g_+} \cdot \exp\left(\frac{KT}{\Phi - IP}\right)} \quad (3)$$

Review of the equations (2) and (3) leads to understanding that a metallic emitter which is disposed to arouse the surface ionization should have the property of effecting heat-decomposition efficiently and have a larger work function, and that the surface ionization is specific to chemical species and is also strongly dependent on ionization potentials possessed by the chemical species.

Thus, in order to selectively detect amonia and amine related compounds, the material of the electrode (as described above) was carefully selected and the work function of the electrode was boosted to the most suitable value of the work function by heating the electrode. For example, a platinum emitter is maintained at a temperature of about 500°-600° C. under atmospheric conditions. The above elements enable the selective and sensitive detection of amonia and amine compounds not possible with the prior art devices.

BEST MODE FOR CARRYING OUT THE INVENTION

The invention will be explained in the following with reference to the drawings.

Figure 1:
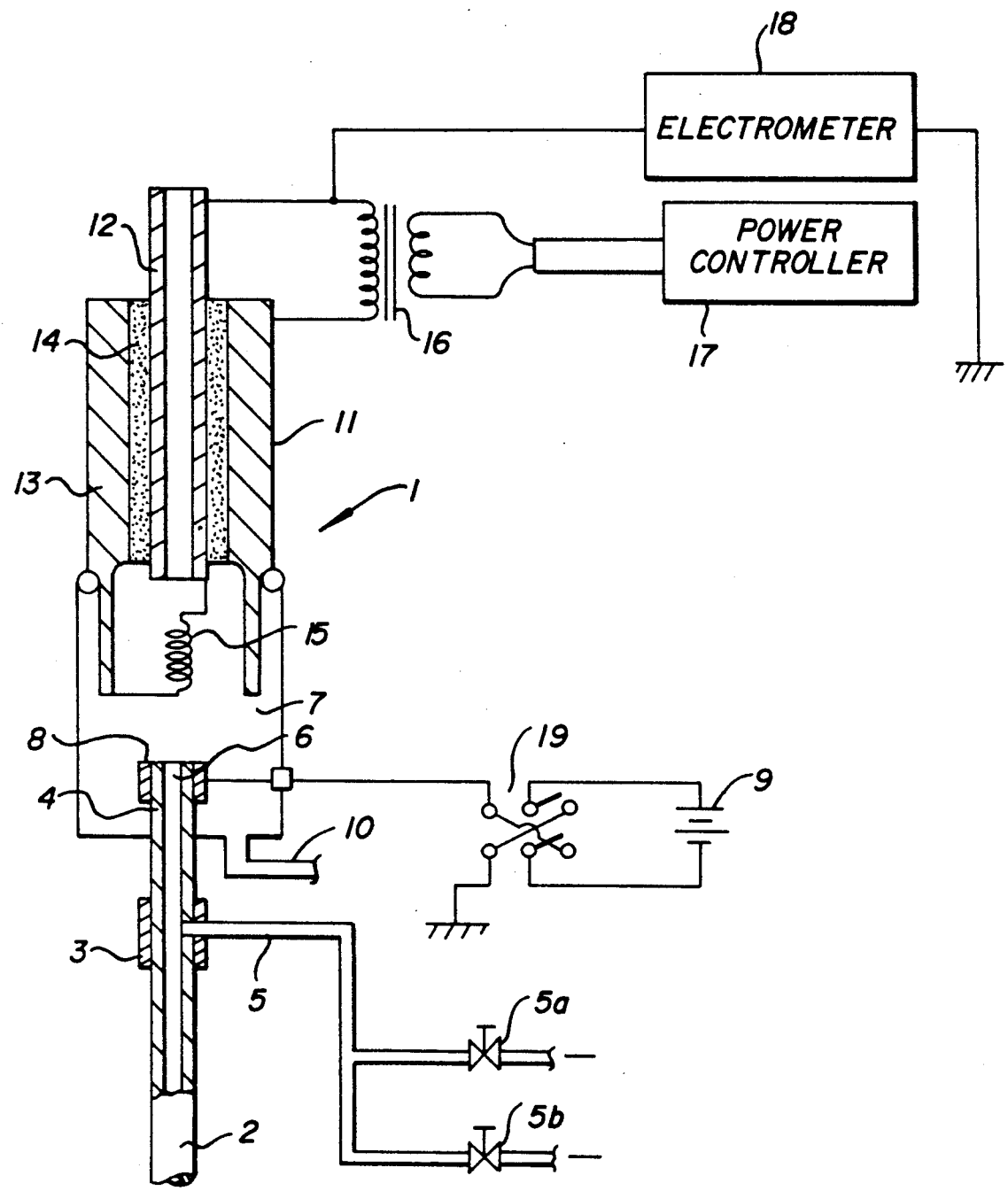
FIG. 1 is a schematic diagram showing an embodiment of the present invention.

Making reference to a detector (1) shown in FIG. 1, a carrier gas exit (outlet of a column) (2) is connected with aid of a T-shaped joint (3) to a quartz-made nozzle (4), and another pipe (5) to be connected to the T-shaped joint (3) is branched and it is connected through stop valves (5a), (5b) to an oxygen or air source and a hydrogen source (these are not shown). An opening (6) of the nozzle (4) is opened in an ionizing chamber (7) and a nozzle electrode (8) is provided around the opening (6) and is in connection to DC source (9) with interposition of a polarity change switch (19). The DC source (9) is generally adequate with a DC supply voltage of 200 to 300 V.

In the neighborhood of the nozzle (4) in the ionizing chamber (7), a pipe for oxygen or air supply (10) is provided. The oxygen or air is meant for maintaining space in the ionizing chamber (7) in an oxidizing atmosphere wherefor the supply pipe (10) is preferably aided with provision of baffle plates to obtain uniform dispersion. In opposing to the nozzle electrode (8) in the ionizing chamber (7), a collector electrode (11) is provided, which is integrally formed with a cylindrical inner collector (12) and a cylindrical outer collector (13) with a ceramic-made insulating cylinder (14) interleaved wherein the outer collector (13) is extending cylindrically inwardly of the chamber to surround the heater emitter electrode (15). The electrode (15) should be a wire, whose surface is covered with oxides of platinum, molybdenum, rhenium or iridium, wherein such oxides may be acceptable, if the oxides have been formed by heating prior to a target measurement. Further, the electrode (15) is connected with its one end to edge of the inner collector (12) and with its the other end to edge of the outer collector (13), and further associated to a power controller (17) via a transformer (16) so that it may be heated to desired temperatures preferably between about 500°-600°C. Specifically noted, the electrode (15) is secured, for instance, at a position of ca. 6 mm apart from the nozzle electrode (8). And one input terminal of the electrometer (18) is connected to secondary side of the transformer (16) which will reach the inner collector electrode (12) while the other terminal thereof is connected to the polarity change switch (19). Based on arrangements as noted above, reference will be made to a case that the detector (1) is used as an SID, for the first place.

Assuming that a sample gas (amine compounds and ammonia) flowing out of the exit (2) of the separation column is directed, upon open of the stop valve (5a), to mix at the T-shaped joint with air which is introduced by the pipe (5). In this step, flow rate of air if preferably 10 to 60 ml/min.

The sample gas mixed with air is distributed into the ionizing chamber (7) by passing the edge of the nozzle (4). The sample gas received in the ionizing chamber (7) is then mixed with air (20 to 100 ml/min.) supplied from the pipe (10) and subjected to contact with the heated electrode (15), which is heated to about 500°-600° C, and then to decompose thermally whereby amine compounds and ammonia are ionized and yield positive ions.

In the step above, if the nozzle electrode (8) is applied with negative polarity of the DC source (9) by action of the polarity change switch (19), the collector electrode (11) becomes positive whereby electrons yielded by cationization will be caught as electron current by the collector electrode (11). Once this electron current is detected by an electrometer (18), it is amplified to be recorded by a recorder (not shown).

Figure 2:
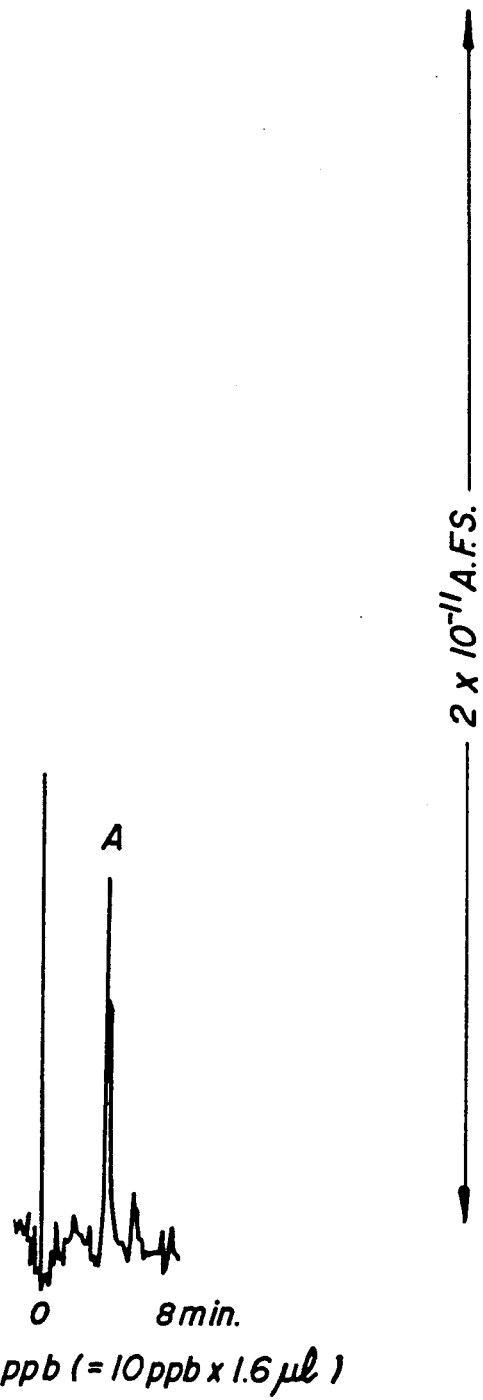
FIGS. 2 and 3 are chromatograms indicating sensitivity and selectivity for amine compounds when a detector as shown in FIG. 1 is used as SID.
Figure 3A:
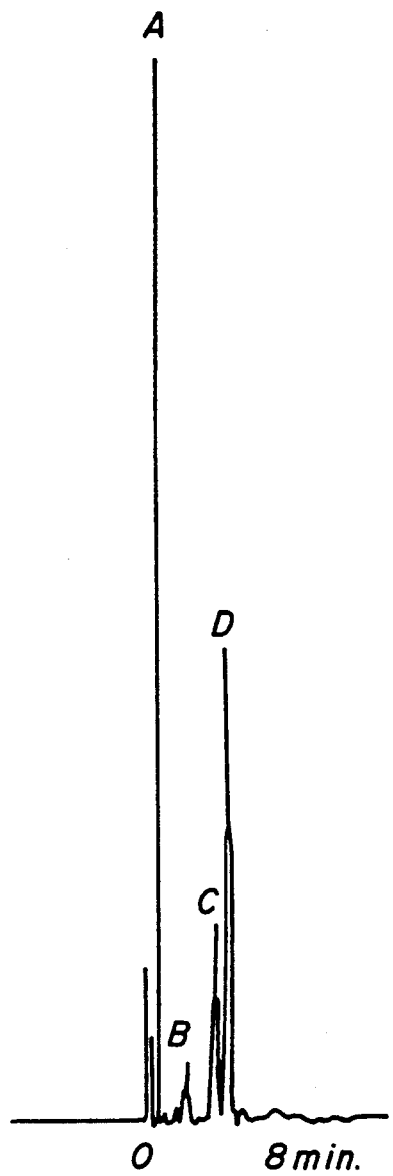
Figure 3B:
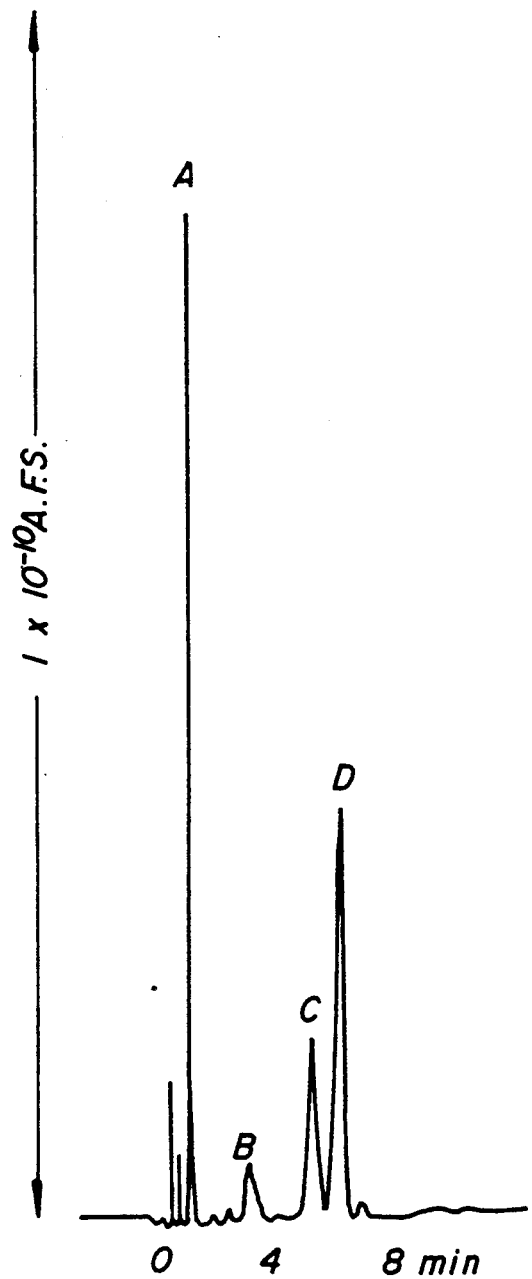

Results of measuring amine compounds and ammonia in those steps as noted above are demonstrated in chromatograms of FIGS. 2 and 3, wherein the abscissa indicates time (min.) while the ordinate does votage (100 scales define 0.01 volt). Analytical conditions involved are as follows:

A test sample used is 1.6 $\mu l$ of acetone solution containing 10 ppb of tri n-butyl amine and the column used is a glass column measuring 2.6 mm in inner diameter and 2 m in length, and packing material used is 80 to 100 mesh of Chromosord W covered with 15% of Apiezon L and 5.0% solution of potassium hydroxide. Temperature of the column is 150° C. and same of the detector is 250° C. Range is $10^{10}\Omega$, full scale gives 0.02 volt and sensitivity is $2 \times 10^{-12}$A. In FIGS. 2 and 3, apparently appearing are peaks of tri n-butyl amine (denoted by A in FIG. 2 and by C in FIG. 3), wherein the peak A of tri n-butyl amine in FIG. 2 indicates 16 pg. and the peaks C in FIG. 3 does 160 pg of tri n-butyl amine while a peak D for n-dodecane indicates presence of 11.6 $\mu g$ of n-dodecane, which appearances show outstanding selectivity.

Figure 4:
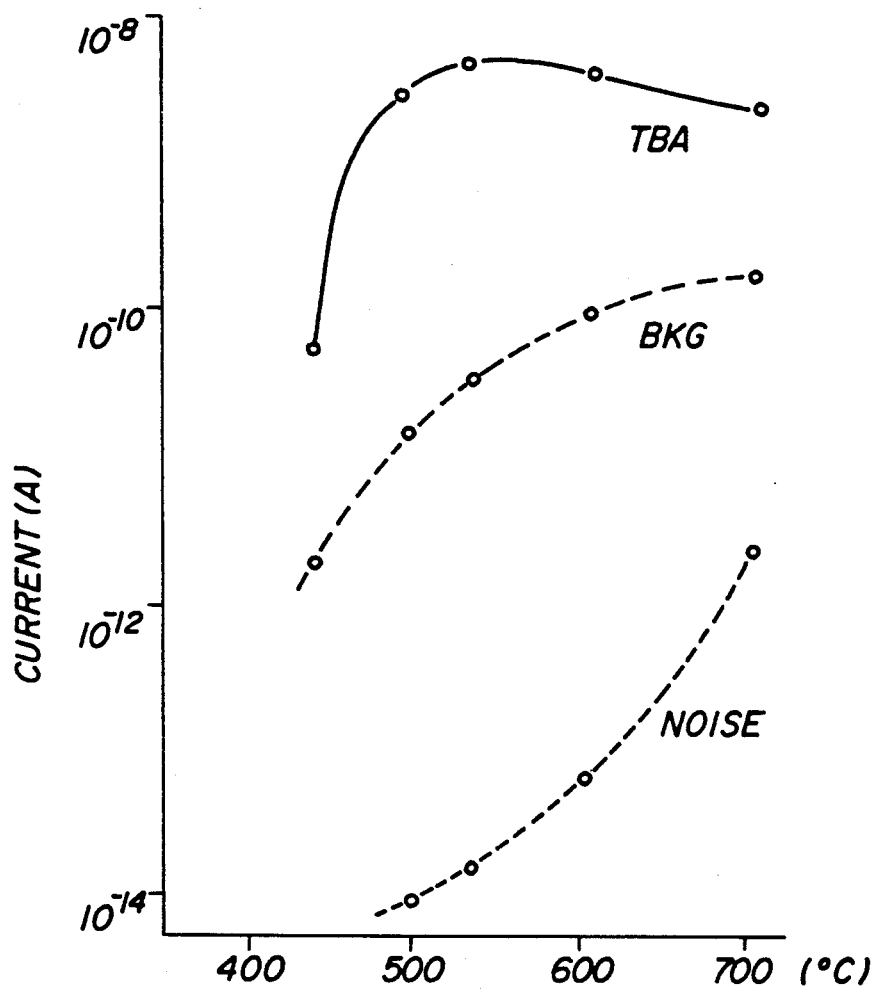
FIG. 4 is a graph illustrating the ionization current at different temperatures.

FIG. 4 illustrates the ionization current compared to the emitter temperature, as practiced by the instant invention. In a sample of 16 ng of tributylamine (TBA) in acetone and under a 40 ml/min. helium carrier with an additional gas of dried air at 20 ml/min., the TBA response (solid line) is charted with respect to the noise current (dotted line) and the background current (BKG—dashed line). It can be clearly seen that the best results occur from about 500°-600° C. The emitter temperature dependence of the TBA response is thus clearly illustrated.

Next reference will be made to the detector device (1) applied as an FID.

Assuming that a sample gas, flowing out of exit of the separation column (2), upon the opening of the stop valve (5b), is directed to the T-shaped joint (3) to mix with hydrogen introduced by the pipe (5), wherein flow rate of hydrogen is preferably 40 to 60 ml/min.

The sample gas mixture with hydrogen is distributed into the ionizing chamber (7), wherein it is then mixed with air introduced by the pipe (10) to contact to the heated electrode (15), whereby automatic firing takes place to give hydrogen flame at the opening (6) of the nozzle (4).

At this moment, if the nozzle electrode (8) is applied with positive polarity of the DC source (9) by action of the polarity change switch (19), the collector electrode (11) becomes negative. As result of combusion of organic compounds by hydrogen flame, positive ions are yielded containing carbon mostly and these ions are caught by the collector electrode (11) and are detected by the electrometer (18). In steps now, platimun of the electrode (15) acts as heating catalyst.

As described in the above, the detector device (1) is capable of two functions as an SID and an FID with ready switching operation.

INDUSTRIAL APPLICABILITY

This invention enables analysis of ammonia, volatile amines etc that are controlled by the Bad Odor Prevention Act, by one analytical operation and further concentration is operationally convenienced. Therefore, this invention will be applied to analysis of polluting compounds, for instance, ammonia and amine compounds present in water and further mine compounds present in living matters with high sensitivity wherein highly reliable analysis is performed with simple analytical operations as connventionally desired.

We claim:

1. A detector device for a gas chromatograph for selectively analyzing ammonia and amine compounds in a sample by subjecting such sample to contact with a heated metallic electrode to form ionized sample components thereon, said device comprising:
    a heated metallic electrode having a larger work function than the ammonia or amine compound in the same component to be analyzed and being maintained at a temperature of 500°-600° C., wherein at least part of the surface of the metallic electrode is formed of a metallic substance selected from the group consisting of platinum, rhenium, iridium, oxides of the three metals, and a combination of said metals with oxides;
    a nozzle for directing sample gases, separated in the gas chromatograph, together with oxygen-containing carrier gases, to contact said heated metallic electrode to form ionized sample components thereon; and
    a pair of electrodes, including a nozzle electrode located at said nozzle and having a negative polarity, and a collector electrode located near said heated metallic electrode, and having a positive polarity.

2. A detector device for a gas chromatograph, for analyzing ammonia and amine compounds in a sample, said device comprising:
    a heated emitter electrode having a larger work function than the ammonia or amine compound in the sample to be analyzed, wherein at least part of the emitter electrode surface is formed of a metallic substance selected from the group consisting of platinum, rhenium, iridium, oxides of the three metals, and a combination of said metals with oxides;
    a heater source connected to said heated emitter electrode for energizing said heated electrode;
    a nozzle disposed opposite said heated electrode for directing sample gas to said heated electrode;
    a sample gas route in communication with said nozzle;
    a plurality of carrier gas flow routes in communication with said nozzle;
    a collector electrode disposed proximal to said heated emitter electrode;
    a nozzle electrode disposed at said nozzle and opposite to said collector electrode; and
    a DC power source connected to said collector and nozzle electrodes, and including means for changing polarity of DC power supplied between said collector and nozzle electrodes, such that when said detector device is used for detecting surface ionization, said collector electrode has a positive polarity and said nozzle electrode has a negative polarity and an oxygen containing gas is supplied to said carrier gas flow routes, and such that when said detector device is used for detecting flame ionization, said collector electrode has a negative polarity and said nozzle electrode has a positive polarity and hydrogen-containing gas is supplied to said carrier gas flow routes.

* * * * *